United States Patent [19]

Gale et al.

[11] Patent Number: 5,614,211
[45] Date of Patent: Mar. 25, 1997

[54] OXYBUTYNIN TRANSDERMAL DEVICE HAVING DECREASED DELAMINATION

[75] Inventors: Robert M. Gale, Los Altos; Eun Soo Lee, Redwood City; Lina T. Taskovich; Terry L. Burkoth, both of Palo Alto, all of Calif.

[73] Assignee: ALZA Corporation, Palo Alto, Calif.

[21] Appl. No.: 481,544

[22] Filed: Jun. 7, 1995

Related U.S. Application Data

[63] Continuation-in-part of Ser. No. 315,043, Sep. 29, 1994.

[51] Int. Cl.6 ................................................. A61F 13/00
[52] U.S. Cl. ............................................ 424/448; 424/449
[58] Field of Search ........................................ 424/448, 449

[56] References Cited

U.S. PATENT DOCUMENTS

| | | | |
|---|---|---|---|
| 4,262,003 | 4/1981 | Urquhart et al. | 424/267 |
| 4,379,454 | 4/1983 | Campbell et al. | 604/897 |
| 4,542,013 | 9/1985 | Keith | 424/28 |
| 4,687,476 | 8/1987 | Pailin | 604/307 |
| 4,784,857 | 11/1988 | Berry et al. | 424/449 |
| 4,817,594 | 4/1989 | Juhasz | 128/155 |
| 4,904,475 | 2/1990 | Gale et al. | 424/449 |
| 4,915,950 | 4/1990 | Miranda et al. | 424/448 |
| 4,938,964 | 7/1990 | Sakai et al. | 424/443 |
| 5,217,718 | 6/1993 | Colley et al. | 424/449 |
| 5,234,690 | 8/1993 | Chiang et al. | 424/448 |
| 5,273,756 | 12/1993 | Fallon et al. | 424/448 |
| 5,298,258 | 3/1994 | Akemi et al. | 424/484 |
| 5,314,694 | 5/1994 | Gale | 424/448 |
| 5,411,740 | 5/1995 | Lee et al. | 424/448 |

FOREIGN PATENT DOCUMENTS

| | | |
|---|---|---|
| 0413487 | 2/1991 | European Pat. Off. . |
| 0607434 | 3/1993 | European Pat. Off. ..... A61K 31/215 |
| WO9210231 | 6/1992 | WIPO . |
| WO9303694 | 3/1993 | WIPO . |
| WO9323025 | 11/1993 | WIPO . |
| WO9421262 | 9/1994 | WIPO . |
| WO9509006 | 4/1995 | WIPO . |
| WO9509007 | 4/1995 | WIPO . |

*Primary Examiner*—D. Gabrielle Phelan
*Attorney, Agent, or Firm*—Michael J. Rafa; Paul L. Sabatine; Steven F. Stone

[57] ABSTRACT

A device for the transdermal administration of oxybutynin comprising a microporous tie layer located between the oxybutynin reservoir and the contact adhesive. The tie layer eliminates blooming and delamination and has no appreciable adverse effect on either the oxybutynin flux or release rate from the device.

22 Claims, 5 Drawing Sheets

OXYBUTYNIN TRANSDERMAL DEVICE HAVING DECREASED DELAMINATION

This application is a continuation-in-part of Ser. No. 08/315,043 filed Sep. 29, 1994, of which the benefit of the earlier filing date is claimed.

TECHNICAL FIELD

This invention relates to medical devices for delivering oxybutynin to the body through intact skin having decreased blooming and delamination at the interface of the contact adhesive and the oxybutynin reservoir layer of the medical device without affecting the oxybutynin flux and release rate from the therapeutic transdermal system. This invention also relates to improved oxybutynin transdermal delivery devices using permeation enhancer mixtures which provide greater oxybutynin skin fluxes and systems which are more easily characterized.

BACKGROUND ART

Devices that deliver drugs through skin for absorption into the body are known in the art. For example, U.S. Pat. No. 4,915,950 to Miranda et al, describes a transdermal drug delivery device including an absorbent source layer laminated to a pressure sensitive pharmaceutically acceptable contact adhesive. The source layer has an anchor adhesive layer laminated to its opposing side and a drug-impermeable backing layer applied to the anchor adhesive.

U.S. Pat. No. 4,817,594 to Juhasz, describes an integral anti-bacterial wound dressing containing the following five layers: the first layer of a permeable material; a layer of semipermeable material; a layer of electrically-conducted material in the form of an open mesh; a layer of charcoal fabric; and a non-adherent wound facing second layer of a permeable material.

U.S. Pat. No. 4,687,476 to Pailin, describes a continuous multi-layer strip used as a topical dressing, wherein the strip has a continuous layer of a first foil and on one side thereof a laminated material comprising a layer of skin adhesive protected with a release film.

U.S. Pat. No. 4,542,013 to Keith, describes a trinitroglycerol-containing substantially disaccharide-free polymeric diffusion matrix for transdermal systemic delivery of trinitroglycerol. The bandage may also include a facestock layer with skin adhesive, which comprises a foam, film-type, non-woven or vinyl tape with an acrylic, silicon or rubber adhesive.

U.S. Pat. No. 5,217,718 to Colley et al, describes a therapeutic system for the transdermal administration of dexmedetomidine that is a laminated composite of a backing layer, an optional anchor adhesive layer, a contact adhesive layer; and one or more additional layers. The composite also preferably contains an optional porous intermediate layer between the anchor and contact adhesive layer, wherein, when an anchor is included, it is typically an absorbent, non-woven fabric.

U.S. Pat. No. 5,298,258 to Akemi et al, describes an acrylic oily gel bioadhesive material comprising a substrate having on one surface thereof, a crosslinked gel layer.

U.S. Pat. No. 4,938,964 to Sakai et al, describes a formulation which may be applied using a conventional support. A cotton or non-woven fabric may be used for the support.

U.S. Pat. No. 4,904,475 describes a porous support structure for use in a device for delivering ionized drugs from an aqueous reservoir.

U.S. Pat. No. 5,411,740 describes the transdermal administration of oxybutynin and related compounds for the treatment of neurogenic bladder disease, among other things. (All of the aforementioned U.S. Patents are incorporated herein in their entirety by reference.)

In addition, Black "Transdermal Drug Delivery Systems", US Pharmacist, November 1982, pp 49–78, provides additional background information regarding commercially available transdermal drug delivery systems. A reasonably complete summary of the factors involved in percutaneous absorption of drugs may be found in Arita, et al, "Studies on Percutaneous Absorption of Drugs", *Chem. Phar. BUll.*, Vol. 18, 1970, pp 1045–1049; Idson, "Percutaneous Absorption", *J. Phar. Sci.*, Vol. 64, No. 6, pp 910–922; and Clooney, *Advances in Biomedical Engineering*, Part I, Chapter 6, "Drug Permeation Through Skin: Controlled Delivery For Topical or Systemic Therapy", Marcel Dekker, Inc., New York and Basel, 1980, pp 305–318.

Although the transdermal drug delivery route is rapidly becoming a preferred delivery route for a wide variety of drugs, transdermal delivery is not without its problems. In general, direct contact of an adhesive with a drug reservoir which contains an amphipathic molecule, eg, a non-ionic surfactant such as a permeation enhancer, eg, a monoglyceride, ie, glycerol monolaurate or glycerol monooleate, has a problem of blooming at the interface of the contact adhesive/drug reservoir. The occurrence of blooming is caused by the surfactant migrating to the relatively lower energy interface generated by laminating an adhesive to the reservoir. The interface then swells or blooms, causing delamination between the contact adhesive and drug reservoir.

Additionally, the use of a permeation enhancer in any transdermal drug delivery device necessarily complicates the design and development of the device. Permeation enhancers cause compatibility problems throughout the delivery system. Instead of having to characterize the properties of the reservoir compositions, adhesives, and release-controlling materials with respect to just the drug, these materials must now have the proper characteristics with respect to both the drug and the permeation enhancer. Typically, drugs and permeation enhancers have very different physical and chemical properties, and, in most cases, the properties of mixtures of the drug with the permeation enhancer is unknown. For example, permeation enhancers can cause, among other problems, cohesive failure of adhesive and can partition through other components in the system.

DISCLOSURE OF THE INVENTION

It is accordingly an aspect of this invention to provide an improved oxybutynin delivery system containing amphipathic molecules in the oxybutynin reservoir having reduced blooming and delamination at the interface of the contact adhesive and oxybutynin reservoir.

It is another aspect of the invention to provide an improved transdermal oxybutynin delivery device for use with an amphipathic molecule such as a non-ionic surfactant having a microporous tie layer interconnecting the oxybutynin reservoir and contact adhesive.

It is yet another aspect of the invention to provide an improved transdermal oxybutynin delivery device having a microporous tie layer interconnecting the oxybutynin reservoir and contact adhesive which does not affect the flux or the oxybutynin release profiles of the therapeutic transdermal system and which reduces the occurrence of blooming and delamination at the interface of the oxybutynin reservoir and contact adhesive.

Still another aspect of the invention is to provide an improved transdermal oxybutynin delivery device with a permeation enhancer or enhancer mixture that improves the transdermal permeation rate of oxybutynin.

It is yet another aspect of the invention to provide an improved transdermal oxybutynin delivery device with a permeation enhancer or enhancer mixture that provides a system that is more easily characterized.

These and other aspects and advantages of this invention will be readily apparent from the following description with reference to the accompanying figures.

MODES FOR CARRYING OUT THE INVENTION

As used herein, the term "transdermal" delivery or administration refers to the delivery or administration of oxybutynin by passage through skin, mucosa, and/or other body surfaces by topical application.

As used herein, the term "therapeutically effective" amount or rate refers to the amount or rate of oxybutynin needed to effect the desired therapeutic result.

As used herein, the term "oxybutynin" is used to designate oxybutynin, the base, optically resolved oxybutynin, and the related compounds (eg, salts) thereof. Oxybutynin is a base capable of forming acid addition salts with organic and mineral acids, for example, with hydrochloric acid to form oxybutynin chloride. The preferred active agent according to the present invention is oxybutynin in its free base form.

As used herein "amphipathic" molecule refers to an unsymmetrical molecule having one end being hydrophilic and the other end hydrophobic, including, for example, non-ionic surfactants.

As used herein, the term "non-ionic surfactant" refers to a non-ionic agent which has the effect of altering the interfacial tension of water and other liquids or solids, for example, a monoglyceride. Surfactants may be used as a permeation enhancer for drug transport across skin.

As used herein, the term "monoglyceride" refers to glycerol monooleate, glycerol monolaurate, and glycerol monolinoleate, or a mixture thereof. Monoglycerides are generally available as a mixture of monoglycerides, with the mixture deriving its name from the monoglyceride present in the greatest amount.

As used herein, the term "glycerol monolaurate" refers to glycerol monolaurate itself or a mixture of glycerides wherein glycerol monolaurate is present in the greatest amount.

As used herein, the term "lactate ester" or "lactic ester of an alcohol" refers to ethyl lactate, lauryl lactate, myristyl lactate, cetyl lactate, or a mixture thereof.

Figure 1:
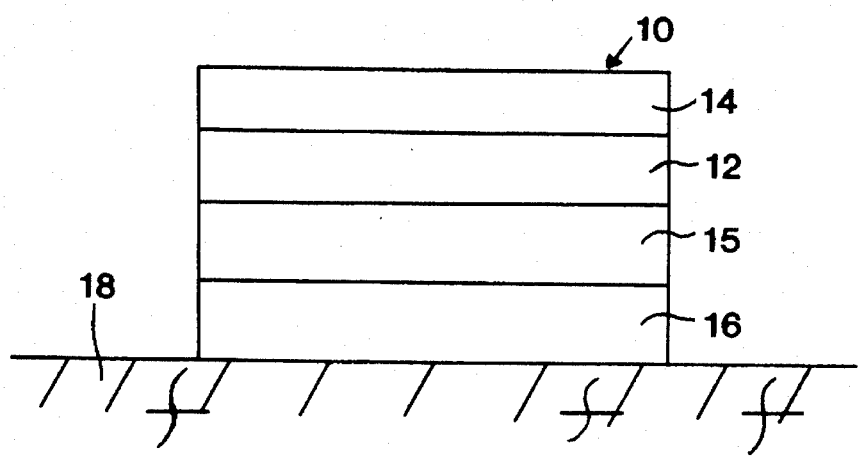
FIG. 1 is a cross-sectional view of one embodiment of the transdermal drug delivery system according to this invention.

Referring now to FIG. 1, a preferred embodiment of a transdermal delivery device 1, according to this invention is shown. The system is specifically adapted to reduce the problem of blooming and delamination of the contact adhesive from the oxybutynin reservoir layer when the oxybutynin reservoir contains a non-ionic surfactant. The blooming and delamination problems are eliminated or reduced by including a microporous tie layer between the oxybutynin reservoir layer and the contact adhesive. In FIG. 1, transdermal delivery device 10, comprises a reservoir containing both oxybutynin and a permeation enhancing mixture. Reservoir 12 is preferably in the form of a matrix containing oxybutynin and permeation enhancer mixture dispersed therein. Reservoir 12 is sandwiched between a backing layer 14 and a microporous tie layer 15. Preferably, the backing layer 14 is a spun-laced polyester, such as Sontara®, a nylon reinforced polyurethane, such as NRU-100-C Flexcon®, or a multilaminate film layer, such as PE/EVA/polyvinyldienefluoride/EVA/PE film layer Saranex® (Dow Chemical Co.). On the other side of the tie layer 15 is the in-line contact adhesive layer 16. The device 10 adheres to the surface of the skin 18, by means of the adhesive layer 16. The adhesive layer 16 may optionally contain the permeation enhancing mixture and/or oxybutynin. A strippable release liner (not shown in FIG. 1) is normally provided along the exposed surface of the adhesive layer 16 and is removed prior to application of device 10 to skin 18.

Figure 2:
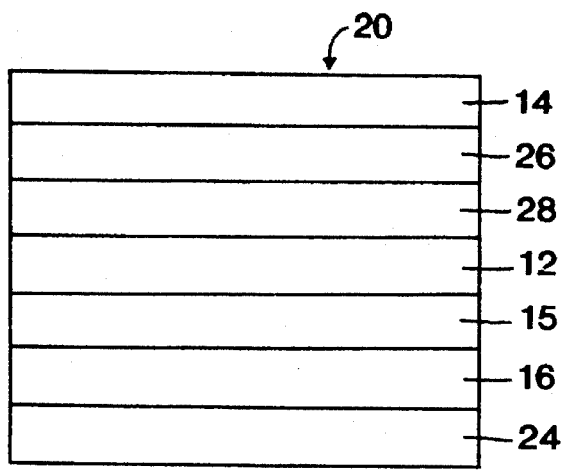
FIG. 2 is a cross-sectional view of another embodiment of the transdermal drug delivery system of this invention.

In FIG. 2, transdermal delivery device 20, comprises an oxybutynin- and permeation enhancing mixture-containing reservoir ("oxybutynin reservoir") 12 substantially as described with respect to FIG. 1. Permeation enhancer reservoir ("enhancer reservoir") 26 comprises the permeation enhancing mixture dispersed throughout and is substantially free of any undissolved oxybutynin. The enhancer reservoir 26 may contain the oxybutynin at or below saturation. Enhancer reservoir 26 is preferably made from the same matrix as is used to form oxybutynin reservoir 12. Rate-controlling membrane 28 for controlling the release rate of the permeation enhancer from enhancer reservoir 26 to oxybutynin reservoir 12 is placed between the two reservoirs.

Superimposed over the permeation enhancer mixture 26 of device 20 is a backing 14 that is permeable to water vapor. On the skin proximal side of reservoir 12 are a microporous tie layer 15; an adhesive layer 16, and a strippable liner 24 which would be removed prior to application of the device to the skin.

The purpose of the tie layer 15 is to reduce blooming and delamination at the oxybutynin reservoir 12 and contact adhesive interface 16 but not to affect the flux or the release rate profiles of the oxybutynin from therapeutic transdermal systems. Potential tie layers are formed from materials that have a low or negligible solubility of the amphipathic molecule and oxybutynin and should have a porous or open structure so that the oxybutynin flux, as well as oxybutynin release rates, are not affected by the tie layer. Useful tie layers include but are not limited to microporous polypropylene membranes, microporous polyethylene membranes, porous polycarbonate, and spunbonded filamentous materials. The main defining characteristic of the tie layer is that it be formed of a material that does not absorb either the amphipathic molecule or oxybutynin and is sufficiently open to allow transport of oxybutynin and permeation enhancer.

The device is constructed so that the oxybutynin reservoir and/or adhesive layer when laminated on either side of the tie layer fills in the space defined by the open spaces in the tie layer.

In the embodiments of FIGS. 1 and 2, the carrier or matrix material of the reservoirs has sufficient viscosity to maintain its shape without oozing or flowing. If, however, the matrix or carrier is a low-viscosity flowable material such as a liquid or gel, the composition may be fully enclosed in a pouch or pocket as known to the art from U.S. Pat. No. 4,379,454, for example, and is illustrated in FIG. 3.

Figure 3:
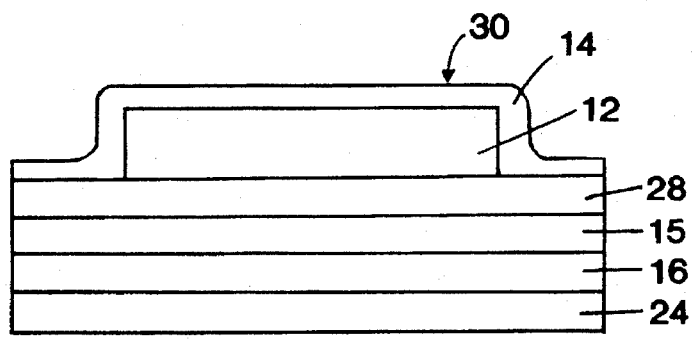
FIG. 3 is a cross-sectional view of still another embodiment of the transdermal drug delivery system according to this invention.

Device 30 in FIG. 3 comprises a backing member 14 which serves a protective cover for the device, imparts structural support, and substantially keeps components in device 30 from escaping from the device. Device 30 also includes a reservoir 12 which contains oxybutynin and the permeation enhancer mixture, in low viscosity flowable form (eg, a liquid of gel form), and bears on its surface distant from the backing member 14, a rate-controlling membrane 28, for controlling the release of the oxybutynin and/or permeation enhancer mixture from device 30. The outer edges of the backing member overlay the edges of reservoir 12 and are joined along the perimeter with the outer edges of the rate-controlling membrane 28 in a fluid-tight arrangement. This sealed reservoir may be effected by pressure, fusion, adhesion, and adhesive applied to the edges, or other methods known in the art. In this manner, reservoir 12 is contained only between backing member 14 and rate-controlling membrane 28. On the skin-proximal side of rate-controlling membrane 28 are a microporous tie layer 15; an adhesive layer 16; and a strippable liner 24, respectively. The strippable liner 24 would be removed prior to application of the device 30 to the skin.

In an alternative embodiment of device 30 of FIG. 3, reservoir 12, contains the permeation enhancing mixture only and is substantially free of any undissolved oxybutynin. Oxybutynin at or above saturation and an additional amount of permeation enhancer mixture are present in the adhesive layer 16 which acts as a separate reservoir.

The formulation to be contained in the oxybutynin reservoir of device 30 is non-aqueous based and designed to deliver oxybutynin and permeation enhancer mixture at necessary fluxes. Typical non-aqueous gels are comprised of silicon fluid or mineral oil. Mineral oil-based gels also typically contain 1–2 wt % of a gelling agent such as colloidal silicon dioxide. The suitability of a particular gel depends upon the compatibility of its constituents with both the oxybutynin and permeation enhancing mixture and any other components in the formulation. The reservoir matrix should be compatible with oxybutynin, permeation enhancer mixture, and any carrier therefore. The term "matrix" as used here refers to well-mixed composite ingredients fixed into shape.

When using a non-aqueous-based formulation, the reservoir matrix is preferably composed of a hydrophobic polymer. Suitable polymeric matrices are well known in the transdermal drug delivery art, and examples are listed in the above-named patents previously incorporated herein by reference. A typical laminated system would comprise a polymeric membrane and/or matrix such as ethylene vinyl acetate (EVA) copolymers, such as those described in U.S. Pat. No. 4,144,317, incorporated herein by reference preferably having a vinyl acetate (VA) content in the range of from about 9% up to about 60% and more preferably from about 9% to 40% VA. Polyisobutylene/oil polymers containing from 4–25% high molecular weight polyisobutylene and 20–81% low molecular weight polyisobutylene with the balance being an oil such as mineral oil or polyisobutenes may also be used as the matrix material.

The amount of oxybutynin present in the therapeutic device and required to achieve an effective therapeutic result depends on many factors, such as the minimum necessary dosage of oxybutynin for the particular indication being treated; the solubility and permeability of the matrix, of the adhesive layer, and the rate-controlling membrane, if present; and the period of time for which the device will be fixed to the skin. The minimum amount of oxybutynin is determined by the requirement that sufficient quantities of oxybutynin must be present in the device to maintain the desired rate of release over the given period of application. The maximum amount for safety purposes is determined by the requirement that the quantity of oxybutynin present cannot exceed a rate of release that reaches toxic levels. The oral lethal dose for rats is 1220 mg/kg.

The range of desired and achievable system permeation rates of oxybutynin through skin, desired therapeutic blood levels, and administration rates are described in U.S. Pat. No. 5,411,740, incorporated herein in its entirety by reference. For example, therapeutic blood levels of oxybutynin from about 0.5 ng/ml to about 3.0 ng/ml can be obtained from administration rates in the range of 0.08 mg/hr to 0.5 mg/hr. Representative in vitro skin permeation rates of oxybutynin through living human skin are in the range of about 1 $\mu g/cm^2$ hr to about 40 $\mu g/cm^2$ hr, depending upon the permeation enhancer. The dose of oxybutynin which can be delivered transdermally is preferably about 1–20 mg over a 24 hour period.

The oxybutynin is normally present in the matrix or carrier at a concentration in excess of saturation, the amount of excess being a function of the desired length of the oxybutynin delivery period of the system. The oxybutynin may, however, be present at a level below saturation without departing from this invention as long as oxybutynin is continuously administered to the skin or mucosal site in an amount and for a period of time sufficient to provide the desired therapeutic rate.

The permeation enhancing mixture is dispersed throughout the matrix or carrier, preferably at a concentration sufficient to provide permeation-enhancing amounts of enhancer in the reservoir throughout the anticipated administration period. Where there is an additional, separate permeation enhancer matrix layer as well, as in FIG. 3, the permeation enhancer normally is present in the separate reservoir in excess of saturation.

It may be preferable when using a monoglyceride as the permeation enhancer to provide a second permeation enhancer or cosolvent. Suitable cosolvents should be compatible with oxybutynin and provide enhanced skin permeation without causing blooming or delamination of the oxybutynin reservoir—contact adhesive interface. Preferred cosolvents or additional enhancers include, but are not limited to, lactate esters or lactic esters of an alcohol such as ethyl lactate, myristyl lactate, cetyl lactate, or a mixture thereof, Ceraphyl® 31 (50.6% lauryl lactate, 19.1% myristyl lactate, 8.8% lauryl alcohol, 8.3% palmityl lactate, 3.7% stearyl lactate, and 3.5% myristyl alcohol), a purer lauryl lactate (82.8% lauryl lactate, 11% lauryl lactyllactate, and 4% 1-dodecanol), methyl laurate, and lauryl acetate, alone or in combinations of one or more. Cosolvents obtainable at a high degree of purity, such as lauryl acetate, are preferable since they provide more stable formulations and systems which are more easily characterized.

In addition to the oxybutynin and permeation enhancer mixture, which are essential to the invention, the matrix or carrier may also contain dyes, pigments, inert fillers, excipients, and other conventional components of pharmaceutical products for transdermal devices known in the art.

Because of the wide variation in skin permeability from individual to individual and from site to site on the same body, it is preferable that the oxybutynin and permeation enhancer mixture be administered from a rate-controlled transdermal delivery device. Rate control can be obtained through either an adhesive or through other means. A certain amount of oxybutynin will bind reversibly to the skin, and it is accordingly preferred that the skin-contacting layer of the device include this amount of oxybutynin as a loading dose.

The skin-contacting surface area of the device of this invention can vary from less than 1 cm$^2$ to greater than 200 cm$^2$. A typical device, however, will have a skin-contacting surface area within the range of about 5–50 cm$^2$.

The devices of this invention can be designed to effectively deliver oxybutynin for an extended period of time from several hours up to seven days or longer. Seven days is generally the maximum time limit for application of a single device because the adverse effect of occlusion of a skin site increases with time and a normal cycle of sloughing and replacement of the skin cells occurs in about seven days.

Preferably, the transdermal oxybutynin delivery device contains a sufficient amount of permeation enhancer mixture to provide systemic administration of oxybutynin through the skin for a predetermined period of time for the oxybutynin to provide an effective therapeutic result.

A preferred embodiment of the invention is a device for the transdermal administration of oxybutynin at a therapeutically effective rate comprising:

(a) a reservoir comprising:
 (I) 1–40% by weight oxybutynin,
 (ii) 10–50% by weight of a permeation enhancer or permeation enhancer mixture,
 (iii) 30–90% by weight ethylene vinyl acetate having a vinyl acetate content of 9–60%;
(b) a microporous tie layer on the skin-proximal surface of the reservoir;
(c) a backing on or adjacent the skin-distal surface of the reservoir and permeable to water vapor; and
(d) means for maintaining the reservoir in oxybutynin- and permeation enhancer mixture-transmitting relationship with the skin on the skin-proximal surface of the tie layer.

More preferably, the present invention is a device for the transdermal administration of oxybutynin at a therapeutically effective rate comprising:

(a) a reservoir comprising:
 (I) 10–30% by weight oxybutynin,
 (ii) 10–30% by weight glycerol monolaurate,
 (iii) 5–30% by weight of a cosolvent or second permeation enhancer,
 (iv) 30–70% by weight ethylene vinyl acetate having a vinyl acetate content of 9–40%;
(b) a microporous tie layer on the skin-proximal surface of the reservoir;
(c) a backing on or adjacent the skin-distal surface of the reservoir and permeable to water vapor; and
(d) means for maintaining the reservoir in oxybutynin- and permeation enhancer mixture-transmitting relationship with the skin on the skin-proximal surface of the tie layer.

The aforementioned patents describe a wide variety of materials which can be used for fabricating the various layers and components of the transdermal oxybutynin delivery devices according to this invention. This invention, therefore, contemplates the use of materials other than those specifically disclosed herein, including those which may hereafter become known to the art and to be capable of performing the necessary functions.

The following example is offered to illustrate the practice of the present invention and is not intended to limit the invention in any manner.

EXAMPLE 1

The oxybutynin/permeation enhancer reservoir was prepared by mixing ethylene vinyl acetate copolymer having a vinyl acetate content of 40 percent ("EVA 40", U.S.I. Chemicals, Illinois) in an internal mixer (Brabender type mixer) until the EVA 40 pellets fused. Oxybutynin, glycerol monolaurate, and Ceraphyl 31 (ISP Van Dyk, Bellevue, N.J.) were then added. The oxybutynin/enhancer reservoir formulation is shown in Table 1.

The mixture was blended, cooled, and calendered to a 5 mil thick film. The film was then laminated to an acrylic contact adhesive (MSPO41991P, 3M, St. Paul, Minn.) on one side and a Medpar (3M) backing on the opposite side. The system was then tested with and without a Celgard® (Hoescht Celanese, Charlotte, N.C.) microporous polypropylene membrane which, when present, was laminated between the reservoir and adhesive. The laminate was then cut into 1.98 cm$^2$ circles using a stainless steel punch.

TABLE 1

| Drug/Permeation Enhancer Reservoir Composition (weight percent) |
|---|
| Oxybutynin base/GML/Ceraphyl 31/EVA 40 25/20/12/43 |

Circular pieces of human epidermis were mounted on the receptor compartment of horizontal permeation cells with the stratum corneum facing the donor compartment of the cell. The release liner of the system was then removed and the system was centered over the stratum corneum side of the epidermis. The donor compartment was then clamped with the receptor compartment. A known volume of the receptor solution (0.05M sodium phosphate pH 6.0) that had been equilibrated at 35° C. was placed in the receptor compartment. Air bubbles were removed, the cell was capped and placed in a water bath shaker at 35° C.

Figure 4:
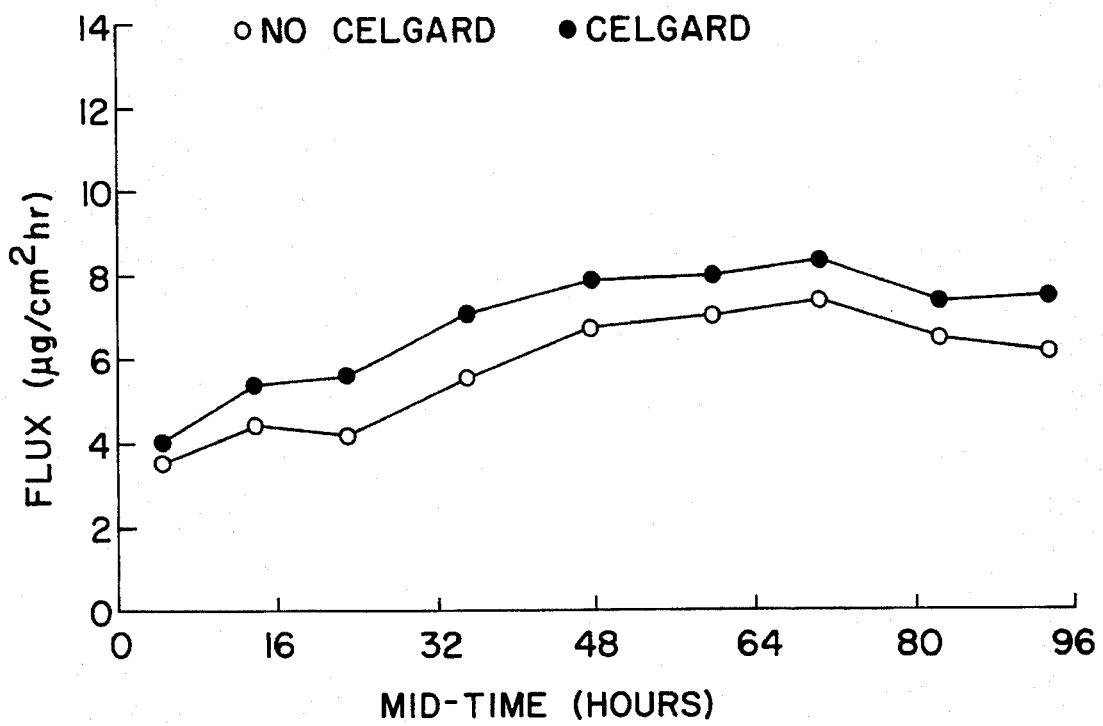
FIG. 4 is a graph of the effect of a microporous polypropylene tie layer on the oxybutynin skin flux.

At given time intervals, the entire receptor solution was removed from the cells and replaced with an equal volume of fresh receptor solution previously equilibrated at 35° C. The receptor solutions were stored in capped vials at 4° C. until assayed for oxybutynin content by high performance liquid chromatography (HPLC). FIG. 4 shows the transdermal fluxes of oxybutynin for the two system types (with and without the Celgard tie layer). As demonstrated in FIG. 4, the oxybutynin skin flux from the system including the Celgard tie layer was greater than that from the system without the tie layer. No blooming or delamination of system components was observed in the systems using the Celgard tie layer.

EXAMPLE 2

The oxybutynin/permeation enhancer reservoir was prepared by mixing ethylene vinyl acetate copolymer having a vinyl acetate content of 40 percent ("EVA 40", U.S.I. Chemicals, Ill.) in an internal mixer (Brabender type mixer) until the EVA 40 pellets fused. Oxybutynin, glycerol monolaurate, Ceraphyl 31, pure lauryl lactate (lauryl lactate) (ISP Van Dyk, Bellevue, N.J.), methyl laurate (Sigma), or dodecyl acetate (lauryl acetate) (Penta International Corp., Livingston, N.J.) were then added as shown in Table 2. The mixture was blended, cooled and calendered to a 5 mil thick film.

TABLE 2

| Drug/Permeation Enhancer Reservoir Composition (weight percent) |
| --- |
| Oxybutynin base/GML/EVA 40 25/20/53 |
| Oxybutynin base/GML/Ceraphyl 31/EVA 40 25/20/12/43 |
| Oxybutynin base/GML/lauryl lactate/EVA 40 25/20/12/43 |
| Oxybutynin base/GML/methyl laurate/EVA 40 25/20/12/43 |
| Oxybutynin base/GML/lauryl acetate/EVA 40 25/20/12/43 |

The drug reservoir film was then laminated to a Sontara® (DuPont, Wilmington, Del.) backing on its skin distal surface and a Celgard microporous polypropylene membrane tie layer on its skin facing surface. An acrylic contact adhesive (MSPO41991P, 3M), if used, was then laminated to the microporous polypropylene tie layer. The laminate was then cut into 1.98 cm² circles using a stainless steel punch and placed in a 35° C. oven to equilibrate. Systems in which an adhesive was used were then masked to prevent any part of the system other than the skin contacting surface to be exposed to the receptor solution when performing the skin flux experiments.

The in vitro transdermal oxybutynin permeation rates through the epidermis of two human skin donors from the systems described above were determined. For each system tested, the release liner was removed and the oxybutynin-releasing surface was centered and placed against the stratum corneum side of a disc of human epidermis which had been blotted dry just prior to use. The excess epidermis was wrapped around the device.

The assembly was then attached to the flat side of a Teflon® holder of a release rate rod using wire and nylon mesh. The rod with the system attached was placed into a 50 cc test tube filled with a known volume of receptor solution (0.05M phosphate solution, pH 6.0). Constant vertical stirring was accomplished by attaching the rod to a crossrod connected to an agitator that reciprocates the rod and system vertically in the test tube. The receptor solution was maintained at 35° C.

Figure 5:
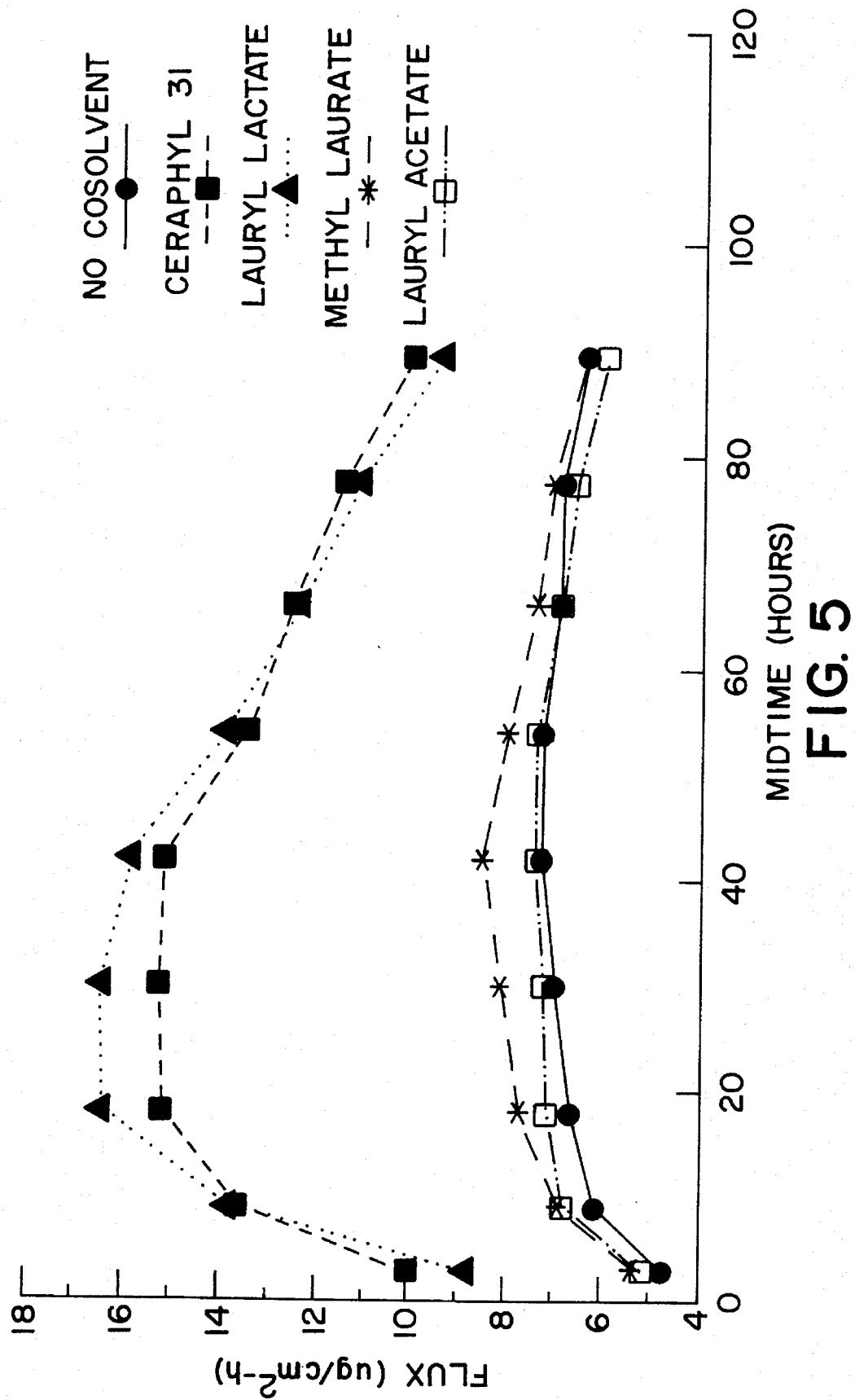
FIG. 5 is a graph of the effect of various cosolvents on the flux of oxybutynin through skin using an acrylate adhesive.
Figure 6:
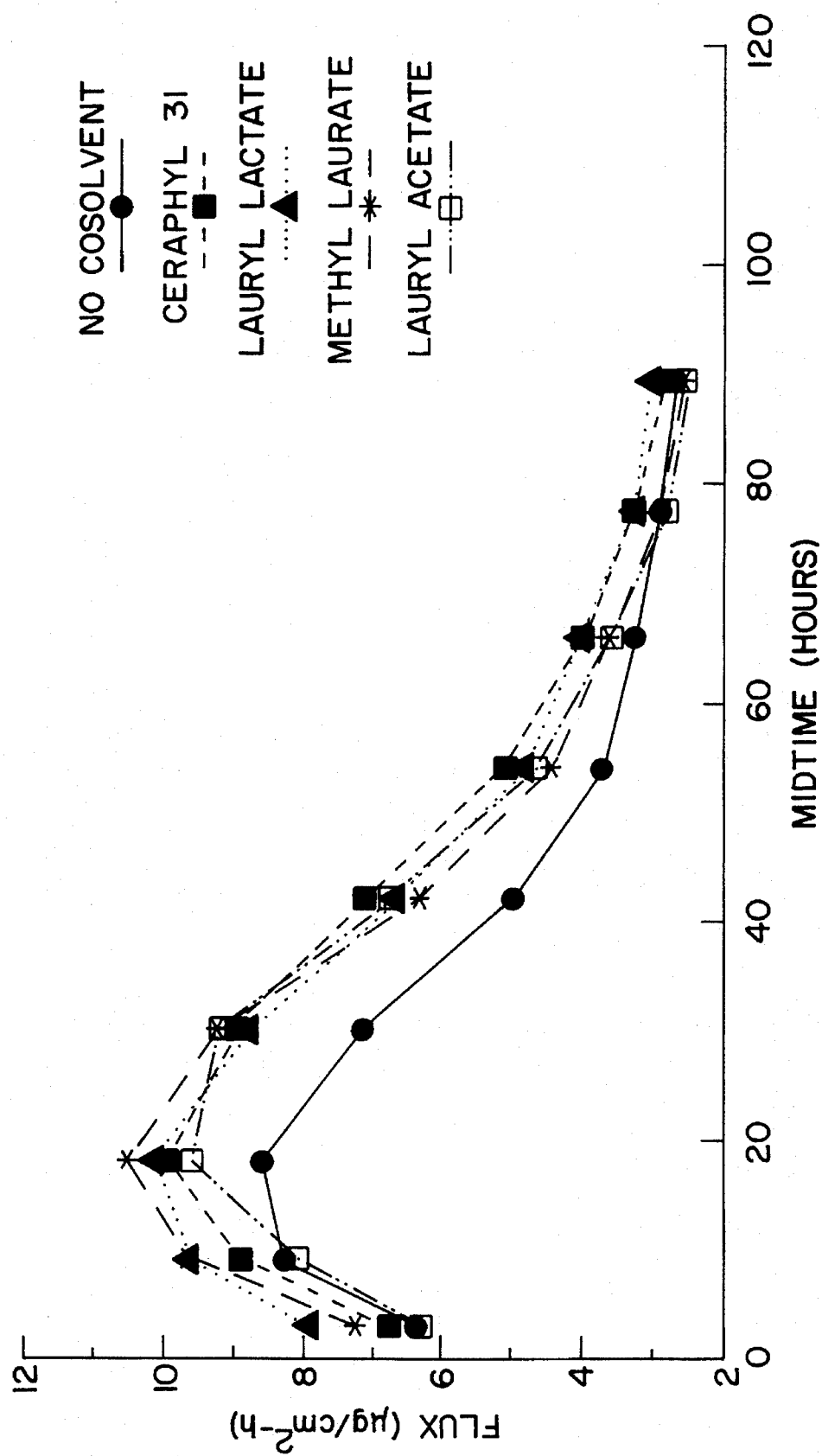
FIG. 6 is a graph of the effect of various cosolvents on the flux of oxybutynin through skin without any adhesive.

At given time intervals, the entire receptor solution was removed from the test tube and replaced with an equal volume of fresh receptor solution previously equilibrated at 35° C. The receptor solutions were stored in capped vials at 4° C. until assayed for oxybutynin content by HPLC. From the drug concentration and the volume of receptor solution, the area of permeation and the time interval, the flux of the drug through the epidermis was calculated as follows: (drug concentration×volume of receptor solution)/(area×time)= flux($\mu g/cm^2$ hr). The fluxes achieved for the different systems are shown in FIGS. 5 and 6. No blooming or delamination of system components was observed.

EXAMPLE 3

Figure 7:
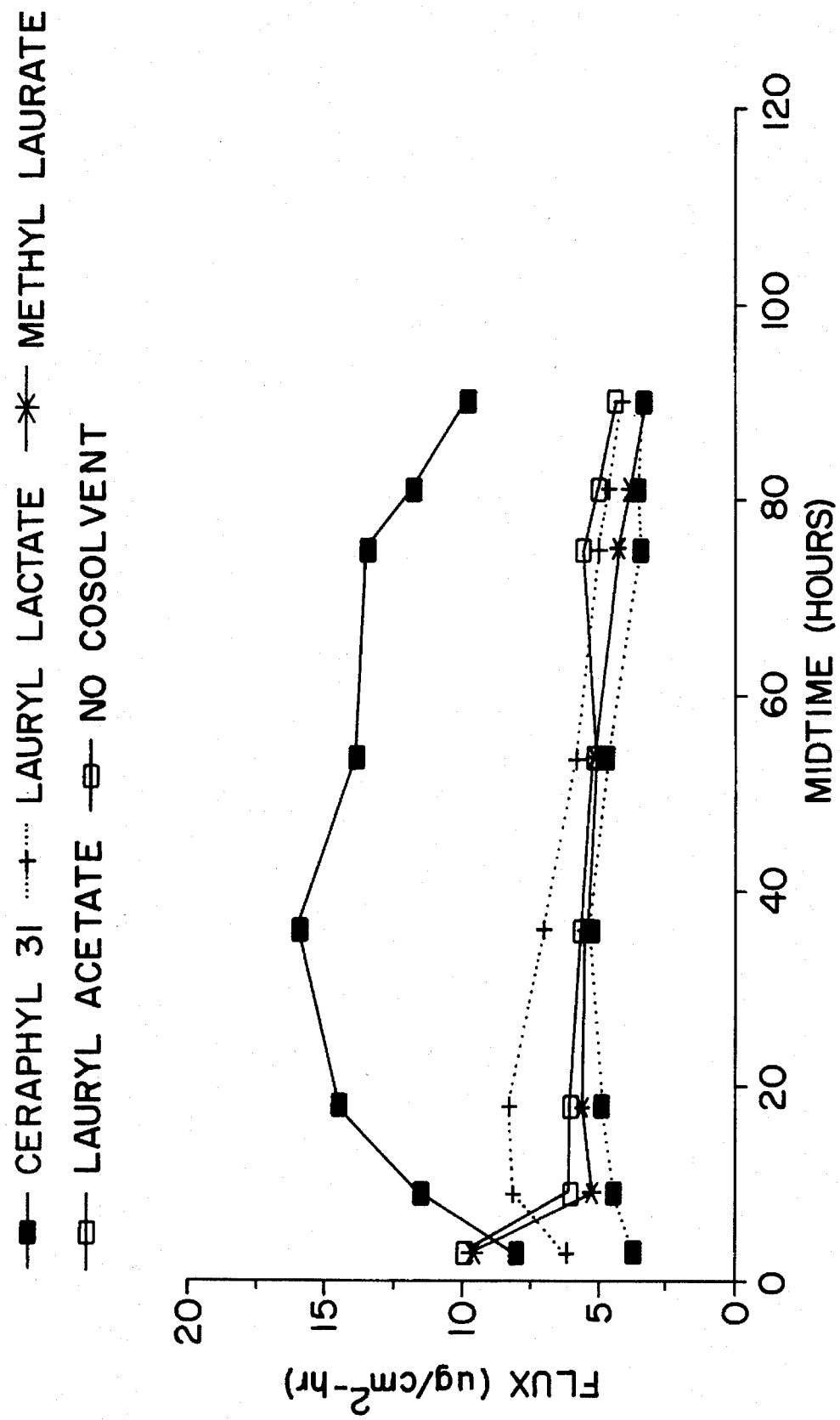
FIG. 7 is a graph of the effect of various cosolvents on the flux of oxybutynin through skin using an acrylate adhesive.

Systems were made following the procedure described in Example 2. An acrylate adhesive, ETA-2 (Adhesive Research, Glen Rock, Pa.) was used in place of the 3M acrylic adhesive of Example 2. The skin flux experiments described in Example 2 were repeated for the formulations comprising the ETA-2 adhesive. FIG. 7 shows the transdermal flux of oxybutynin through human epidermis of a system including GML and various secondary cosolvents with the ETA-2 adhesive.

The invention has been described in detail with particular reference to certain preferred embodiments thereof, but it will be understood that variations and modifications can be affected within the scope and spirit of the invention.

What is claimed is:

1. A device for the transdermal administration of oxybutynin at a therapeutically effective rate, comprising:
   a) a non-aqueous reservoir comprising oxybutynin and a skin permeation-enhancing amount of a permeation enhancer mixture comprising a non-ionic surfactant and a cosolvent;
   b) a non-rate controlling tie layer on the skin-proximal surface of the reservoir, said tie layer being formed from a material having low or negligible solubility for the non-ionic surfactant and oxybutynin and is sufficiently porous so as not to affect, to a rate-controlling extent, the oxybutynin flux or oxybutynin release rate from the device;
   c) a backing on or adjacent the skin-distal surface of the reservoir; and
   d) means for maintaining the reservoir in oxybutynin- and permeation enhancer mixture-transmitting relation with the skin on the skin-proximal surface of the tie layer.

2. A device according to claim 1 wherein the non-ionic surfactant comprises a monoglyceride or mixture of monoglycerides.

3. A device according to claim 2 wherein the monoglyceride is glycerol monolaurate.

4. A device according to claim 2 wherein the cosolvent is selected from the group consisting of methyl laurate, lauryl acetate, or mixtures thereof.

5. A device according to claim 4 wherein the monoglyceride is glycerol monolaurate and the cosolvent is lauryl acetate.

6. A device according to claim 2 wherein the cosolvent comprises a lactic ester or mixture of lactic esters.

7. A device according to claim 6 wherein the monoglyceride is glycerol monolaurate and the lactic ester is selected from the group consisting of lauryl lactate, ethyl lactate, or a mixture thereof.

8. A device according to claim 7 wherein the lactic ester is lauryl lactate.

9. A device according to claim 1 wherein the tie layer is microporous polypropylene.

10. The device according to claim 1 wherein the tie layer is microporous polyethylene.

11. The device according to claim 1 wherein the backing is permeable to water vapor.

12. A device for the transdermal administration of oxybutynin at a therapeutically effective rate, comprising:
   a) a non-aqueous first reservoir comprising oxybutynin and a skin permeation enhancer mixture of a non-ionic surfactant and a cosolvent;
   b) a second non-aqueous reservoir comprising an excess of the permeation enhancer mixture and oxybutynin at or below saturation;
   c) a rate-controlling membrane between the first and second reservoir;
   d) a backing on or adjacent the skin-distal surface of the second reservoir;
   e) a non-rate controlling tie layer on the skin proximal surface of the first reservoir that is formed from a material having low or negligible solubility for the non-ionic surfactant and oxybutynin and is sufficiently porous so as not to affect, to a rate-controlling extent, the oxybutynin flux or oxybutynin release rate from the device; and
   f) means for maintaining the first and second reservoirs in oxybutynin- and permeation enhancer mixture-transmitting relation with the skin on the skin-proximal surface of the tie layer.

13. A device according to claim 12 wherein the permeation enhancer mixture comprises a monoglyceride or mixture of monoglycerides.

14. A device according to claim 13 wherein the monoglyceride is glycerol monolaurate.

15. A device according to claim 13 wherein the cosolvent is selected from the group consisting of methyl laurate, lauryl acetate, and mixtures thereof.

16. A device according to claim 15 wherein the monoglyceride is glycerol monolaurate and the cosolvent is lauryl acetate.

17. A device according to claim 13 wherein the cosolvent comprises a lactic ester or mixture of lactic esters.

18. A device according to claim 17 wherein the monoglyceride is glycerol monolaurate and the lactic ester is selected from the group consisting of lauryl lactate, ethyl lactate, or a mixture thereof.

19. A device according to claim 18 wherein the lactic ester is lauryl lactate.

20. A device according to claim 12 wherein the tie layer is microporous polypropylene.

21. The device according to claim 12 wherein the tie layer is microporous polyethylene.

22. The device according to claim 12 wherein the backing is permeable to water vapor.

* * * * *